United States Patent [19]
Holt et al.

[11] Patent Number: 5,468,453
[45] Date of Patent: Nov. 21, 1995

[54] LOW CARRYOVER PIPETTE PROBE

[75] Inventors: Robert W. Holt, Hackettstown; Thomas Palmieri, Paramus, both of N.J.

[73] Assignee: Cirrus Diagnostics, Inc., Chester, N.J.

[21] Appl. No.: 76,450

[22] Filed: Jun. 14, 1993

[51] Int. Cl.⁶ .......................................... B01L 3/02
[52] U.S. Cl. .................. 422/100; 422/63; 422/99; 436/43; 436/180; 73/864.01; 73/864.14; 73/864.21
[58] Field of Search ..................... 422/63, 65, 67, 422/99, 100; 436/43, 48, 180; 73/864.21, 864.14, 864.01

[56] References Cited

U.S. PATENT DOCUMENTS

| | | | |
|---|---|---|---|
| 3,754,444 | 8/1973 | Ure et al. | 73/423 X |
| 4,312,591 | 1/1982 | Tomoff | 356/315 |
| 4,326,851 | 4/1982 | Bello et al. | 422/63 |
| 4,341,736 | 7/1982 | Drbab et al. | 422/100 |
| 4,818,870 | 4/1989 | Griffiths | 250/288 |
| 5,158,748 | 10/1992 | Obi et al. | 422/100 |
| 5,260,030 | 11/1993 | DeVaughn | 422/100 |
| 5,264,182 | 11/1993 | Sakagami | 73/864.21 |

*Primary Examiner*—Donald E. Czaja
*Assistant Examiner*—Lien Tran
*Attorney, Agent, or Firm*—Whitham, Curtis, Whitham & McGinn

[57] ABSTRACT

An improved pipette probe in an automated chemical analysis system is provided, along with a pipette tip wash protocol to reduce carryover. The pipette tip comprises an elongated stainless-steel barrel which houses a polytetrafluoroethylene tube. The non-wettable properties of polytetrafluoroethylene inhibit fluid adhesion and thereby reduce carryover. The pipette tip is swaged at a fluid dispensing end to a restrictive diameter for good pipetting precision and accuracy. A novel wash protocol is also provided which includes a novel wash solution comprising quantities of Triton X-100 nonionic detergent, Diethanolamine, and NaCl.

4 Claims, 4 Drawing Sheets

LOW CARRYOVER PIPETTE PROBE

CROSS-REFERENCE TO RELATED APPLICATIONS

This patent application is related to the U.S. patent application having the Ser. No. 552,063 filed on Jul. 13, 1990, now U.S. Pat. No. 5,084,240 the U.S. patent application having the Ser. No. 552,132 filed Jul. 13, 1990, now U.S. Pat. No. 5,098,845 and the U.S. Pat. application having the Ser. No. 986,883 filed Dec. 4, 1992, now U.S. Pat. No 5,316,726. All of these applications are herein incorporated by reference.

DESCRIPTION

BACKGROUND OF THE INVENTION

1. Field of the Invention

The present invention generally relates to a pipette probe and, more particularly, to a pipette probe for use in an automated chemical analyzer, such as, for example, an automated immunoassay analyzer.

2. Description of the Prior Art

Many chemical analysis processes involve adding a reagent to a sample, allowing a chemical reaction to occur, and then analyzing the sample to determine its constitutes. An immunoassay is a well known type of chemical analysis method used to determine the amount of an analyte in a sample such as plasma or urine. It is based on the interaction of antibodies with antigens, and because of the degree of sensitivity for the analyte (either antigen or antibody), an immunoassay can be used to quantitatively determine very low concentrations of drugs, hormones, polypeptides, or other compounds found in a test sample.

Chemical analyses, such as immunoassays, were historically performed by hand by a trained laboratory technician. Recently, many companies have begun producing automated analyzers. Such systems are computerized and may utilize a conveyer chain or belt to convey sample vessels from station to station whereat specific analysis steps are carried out. The sample vessels may be bar coded to instruct the computer of its contents and the specific test which is to be performed on each sample. Based on this information, a precise volume of fluid is pipetted from a reagent container or a sample vessel to a test tube with a syringe mechanism.

Depending on the test to be performed, a multitude of reagents may be required. Some tests may even require a combination of several reagents. One way to prevent cross-contamination between samples, has been to use a separate syringe mechanism for each reagent. This is undesirable since it adds greatly to the mechanical complexity of the analyzer and requires an additional wash step for the pipette tip to reduce the level of contamination between the test samples and unspent reagent supply.

An automated immunoassay system must always generate results which are precise, accurate and independent of one another. These criteria are challenging to achieve since, typically laboratory workloads may demand that an automated system generate as many as 120 test results per hour. Although all instrument processes contribute to the instruments ability to produce such results, perhaps none is more important than the pipetting process. As such, it is imperative that the pipette probe be able to transfer liquids precisely and accurately, with virtually no sample-to-sample carryover. Many automated pipette systems in use today employ a standard stainless steel pipette-probe tip available from, for example, the Hamilton Corporation. However, such commercially available tips are largely unsuitable for immunoassay procedures, since they cause an unacceptably high sample to sample carryover rate which leads to distorted, erroneous immunoassay test results.

SUMMARY OF THE INVENTION

It is therefore an object of the present invention to provide a pipette probe for an automated system which has high precision.

It is yet another object of the present invention to provide a pipette probe for an automated chemical analysis system which has accurate sample recovery.

It is yet another object of the present invention to provide a pipette probe for an automated chemical analysis system which can carry out all steps necessary to achieve the aforementioned objects in a very short amount of time.

It is yet another object of the present invention to provide a pipette probe for an automated chemical analysis system which is sufficiently durable to prevent destruction during normal use.

It is yet another object of the present invention to provide a pipette probe which is capable of performing level sensing to minimize exposure of the tip to samples and reagents.

It is yet another object of the present invention to provide a pipette probe for an automated system which is easily replaced by a user.

It is yet another object of the present invention to provide a pipette probe which reduces carryover contamination.

According to the invention, an improved pipette probe, used in an automated chemical analysis system, is provided along with a pipette tip wash protocol. The pipette probe transfers sample fluids and chemical reagents precisely and accurately with minimal carryover contamination from one test vessel or reagent vessel to another. The pipette probe comprises an elongated stainless-steel barrel which houses a polytetrafluoroethylene (Teflon) tube. The stainless steel barrel is coated with polytetrafluoroethylene and provides a robust, electrically conductive structure. Carryover contamination is reduced by several design factors. First, the polytetrafluoroethylene tube and the exterior surface of the barrel are smooth and without seams to discourage fluid drops from lingering and being carried over to the next sample. Second, the non-wettable properties of polytetrafluoroethylene serve to virtually eliminate the formation of carryover drops in the first place. Finally, the pipette tip is swaged at its fluid dispensing end to a restrictive diameter. This contributes to good precision in pipetting small fluid volumes, since any fluid droplets that may be retained at the tip after dispensing would be small in comparison to the total pipetted volume.

A novel wash protocol is used in conjunction with the pipette tip to cleanse the tip and thereby further reduce carry-over contamination. The wash protocol of the preferred embodiment includes several steps, one of which involves using a wash solution comprised of quantities of Triton X-100 nonionic detergent, Diethanolamine, and NaCl.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
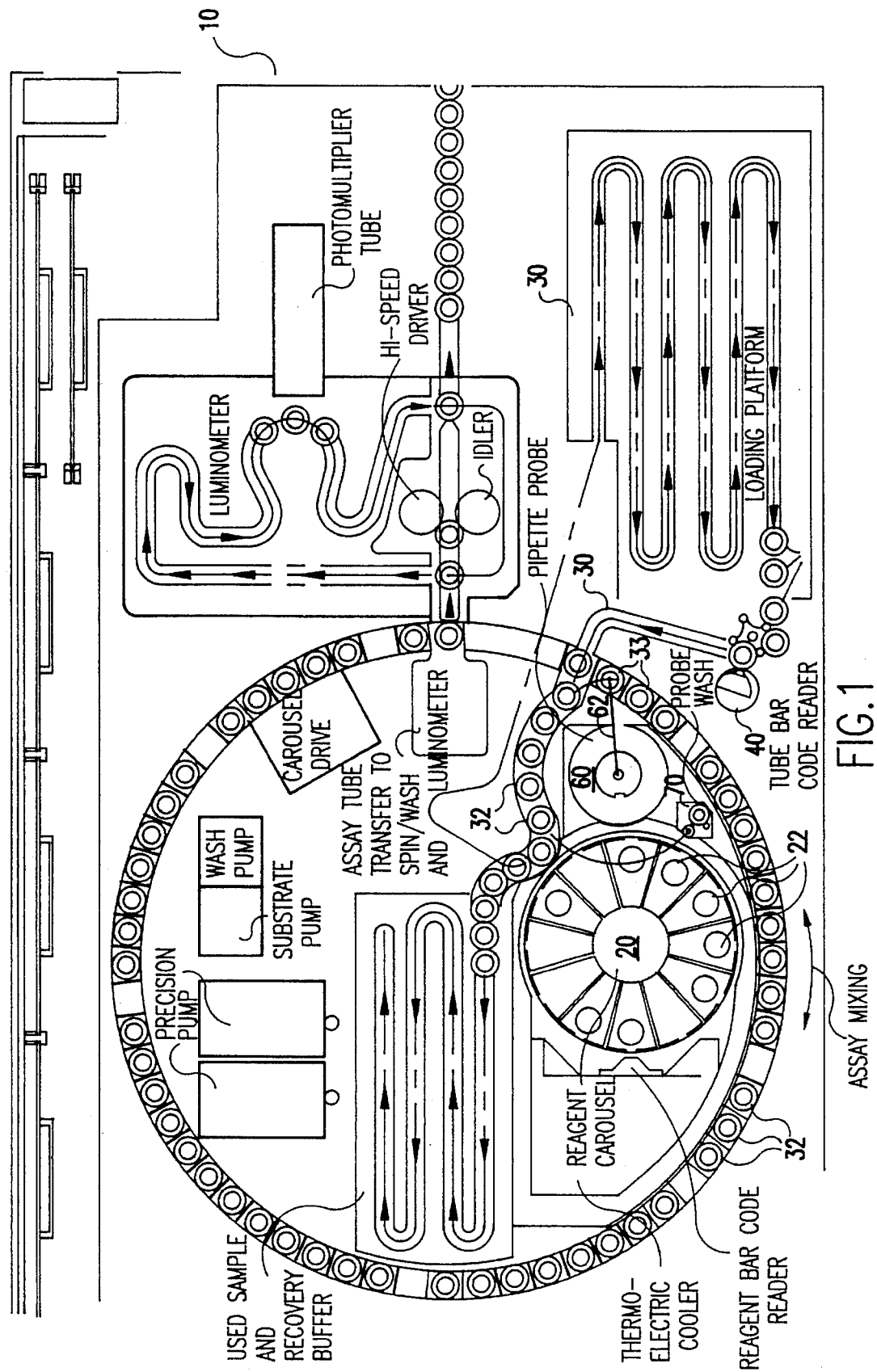
FIG. 1 is schematic showing an automated random access immunoassay analyzer.

Referring now to the drawings, and more particularly to FIG. 1, there is shown a schematic of an automated random access immunoassay analyzer. The analyzer accepts small sample vessels of patient sera, along with assay-specific test units and reagents appropriate to the completion of a wide variety of immunoassays. Through appropriate manipulation of these articles, the instrument produces clinically significant results useful in the quantitation of many heath related parameters.

The automated analyzer, generally referred to by reference numeral 10, incorporates two distinct areas into which the user loads items necessary to instrument function. These include the reagent carousel 20 and the load chain 30. The reagent carousel 20 can accommodate up to twelve different prepackaged liquid reagent units 22, each suitable for the performance of a different immunoassay. The load chain 30 is an endless conveyor which accepts a large number of tubes 32 for testing. The tubes 32 may either be used to carry sample sera or for carrying immunoassays. The tubes 32 are bar-coded and automatically recognized by the analyzer 10 by bar code reader 40. As the chain 30 advances, serum from a sample tube 32, along with the appropriate liquid reagent(s) from the reagent carousel 20, is pipetted into the immunoassay tubes 33 at the pipetting station 60. The pipetting station 60 includes a pipette probe (not shown) projecting downward from an arm 62. The arm 62 travels in a circular path and can access a plurality of tubes 32 as well as reagents 22. Between each pipetting cycle, the pipette probe is washed at wash station 70 to reduce carryover contamination between the reagents 22 and tubes 32.

The pipette tip performance is perhaps the single most important factor contributing to accurate immunoassay test results. The pipette tip performance requirements for an automated immunoassay analyzer, such as that shown in FIG. 1, dictate that pipetting precision must be less than 1% CV, the accuracy greater than 96% sample recovery, the sample to sample carryover must be less than 10 ppm, and it must be fast enough to do all necessary steps in 30 seconds or less. As a practical matter, the pipetting probe must be sufficiently durable to prevent its destruction during normal use and must be easily replaceable by an end user.

Various protocols have been devised, but were unsuccessful in making commercially available pipette probes meet these performance requirements. For example, a commercially available pipette probe, manufactured by the Hamilton Corporation, was attached to the robotic arm 62 of the automated analyzer 10 and evaluated in terms of its ability to meet these performance requirements.

One protocol for fluid pipetting which had the following basic sequence was devised:
Pipetting Protocol A 1) Draw water from the fresh water well
2) Draw liquid reagent from the reagent unit
3) Rinse off excess reagent from the exterior of the tip
4) Draw serum from the sample cup
5) Dispense all of the above into a test unit
6) Insert the tip into a waste sump
7) Wash the tip with 1 mL of water
8) Insert the lower portion of the tip into a blind hole
9) Wash the tip with 2 mL of water In this protocol, the blind hole provides for simultaneous washing of the interior and the exterior surfaces of the pipetting tip. This approach is very significant since it reduces the time required to clean the tip.

Using Protocol A, studies of precision and accuracy via dye testing were conducted. This involved replacing either the reagent or sample with a dye solution of known concentration and then running the pipetting protocol in replicate. For purposes of system evaluation, a sample volume of 10 µL was used because this was the smallest volume the system would ever need to pipette. By measuring the absorbance of the dye in each replicate, pipetting precision was computed as approximately 0.5% CV which is within acceptable limits.

Next the accuracy of the pipette tip was determined by performing the same pipetting steps, in replicate, using highly accurate hand operated pipettes. By comparing the mean absorbance obtained by hand pipettes with that obtained from the Hamilton pipette tip, fluid recovery was determined to be an acceptable 98%.

Finally, the sample to sample carryover was calculated. This is accomplished by using the same pipetting protocol (Protocol A; above) to run an actual immunoassay for the analyte human chorionic gonadotropin (hCG). The following sequence of tubes were loaded into the load chain 30:
Tube 1=Protein buffer containing a very high concentration of hCG
Tube 2=Assay tube for hCG (contents discarded after pipetting)
Tube 3=Sample containing no hCG
Tube 4=Assay tube for hCG Pipetting of the sample in tube 1 into tube 2 serves to contaminate the probe with hCG. The contents of tube 2 are then discarded, and the contents of tube 3 (protein buffer alone) are pipetted into tube 4. This tube is processed normally and hCG concentrations calculated for it. The concentration of hCG found in this tube represents sample to sample carryover. The actual carryover is calculated as:

$$\text{Carryover (ppm)} = ([\text{hCG}] \text{ in tube } 4/[\text{hCG}] \text{ in tube } 1) \times 1{,}000{,}000$$

On a first attempt, the carryover was calculated at 2083 ppm, a figure more than 200 times the acceptable limit. In order to reduce the carryover to an acceptable level, the pipetting protocol was modified by adding a step of flushing the tip with a wash solution intended specifically to cleanse the interior of the tip.

The modified protocols are as follows:
Pitting Protocol B

1) Draw water from the fresh water well
2) Draw liquid reagent from the reagent unit
3) Rinse off excess reagent from the exterior of the tip
4) Draw serum from the sample cup
5) Dispense all of the above into a test unit
6) Insert the tip into a waste sump
7) Wash the tip with 1 mL of wash solution 8) Insert the lower portion the tip into a blind hole 9) Wash the tip with 2 mL of wash solution 10) Wash the tip with 4 mL of water Pipetting Protocol C 1) Draw water from water supply 2) Draw liquid reagent from the reagent unit 3) Rinse off excess reagent from the exterior of the tip 4) Draw serum from the sample cup 5) Dispense all of the above into a test unit 6) Insert the tip into a waste sump 7) Wash the tip with 1 mL of wash solution 8) Insert the lower portion of the tip into a blind hole 9) Wash the tip with 1 mL of wash solution 10) Wash the tip with 2 mL of water These protocols provided for significant reductions in both wash volume and cycle time. As such, all necessary pipetting actions must occur within the requisite 30 seconds.

A variety of wash solutions were evaluated for their effectiveness in reducing carryover. The results were as follows:

| Wash Solution | Carryover, ppm |
|---|---|
| Brine solution<br>3.0 M NaCl | 483 |
| CND solution<br>0.1 mM CTAB cationic detergent<br>50 mM Diethanolamine<br>150 mM NaCl | 357 |
| SND solution<br>0.15% SDS cationic detergent<br>50 mM Diethanolamine<br>150 mM NaCl | not usable |
| BPBS solution<br>0.1% Brij 35 detergent<br>10 mM Sodium phosphate pH 7.4<br>150 mM NaCl | 407 |
| TNaOH solution<br>1.4 mM Triton X-100 nonionic detergent<br>500 mM NaOH | 530 |
| TND solution<br>1.4 mM Triton X-100 nonionic detergent<br>50 mM Diethanolamine<br>150 mM NaCl | 257 |

Based on these results, the TND solution was selected as the best wash solution for the job. Using TND wash solution, sample to sample carryover was reduced about eight fold, and the materials required to produce TND are readily available and inexpensive.

These results also indicated that a portion of the hCG introduced into the tip could be easily removed by washing, while a consistently large remainder was liberated far more slowly since it is sequestered by the interior of the tip. To solve this problem, experiments using two special versions of the Hamilton tip were conducted. One tip had a glass coating on its interior surface and the other had a polytetrafluoroethylene coating. Both were intended to prevent adsorption of hCG onto the stainless steel interior of the tip. Using Protocol "B" described previously, and the TND wash solution, the tips were evaluated and the following results were obtained:

| Tip Coating | Carryover (ppm) |
|---|---|
| Interior glass/exterior polytetrafluoroethylene | 380 |
| Interior polytetrafluoroethylene/exterior polytetrafluoroethylene | 250 |

From this information, it was hypothesized that carryover must result from one of two sources. First, a joint in the fluid path between the tubing and the tip which could contain interstitial spaces might harbor hCG and release it slowly over time. Second, the glass and polytetrafluoroethylene coatings on the experimental tip interiors might be incomplete, so that stainless steel could be exposed on the interior of the tip and contribute to carryover through adsorption.

Figure 2:
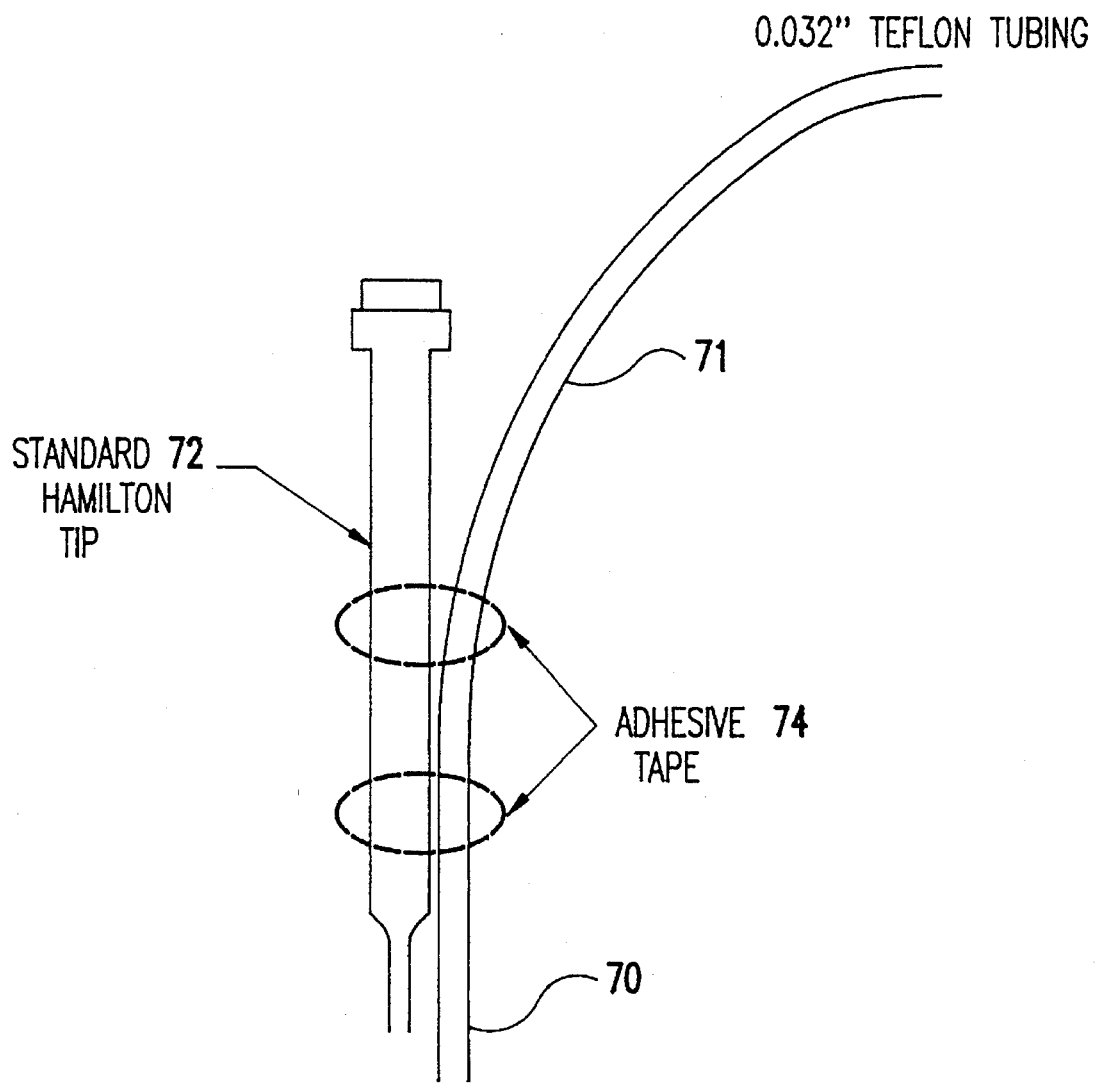
FIG. 2 is a schematic showing an experimental probe comprised of a continuous length of polytetrafluoroethylene tube.

Referring now to FIG. 2, there is shown a modified pipette probe 70 comprised of a single piece of 0.032" polytetrafluoroethylene tubing 71 stiffened by attaching it to the exterior of the standard Hamilton tip 72. This allows the probe 71 to easily attach to the pipetting arm 62 (of FIG. 1) for manipulation; however, only the polytetrafluoroethylene tubing 71 is used for pipetting. A valve connector is used for connecting the tubing 71 to analyzer plumbing. Using pipetting Protocol B, carryover values of 12.5 ppm were obtained, with acceptable precision and accuracy values as well. This preliminary design has obvious limitations, namely, it cannot level sense and is not at all robust.

Figure 3:
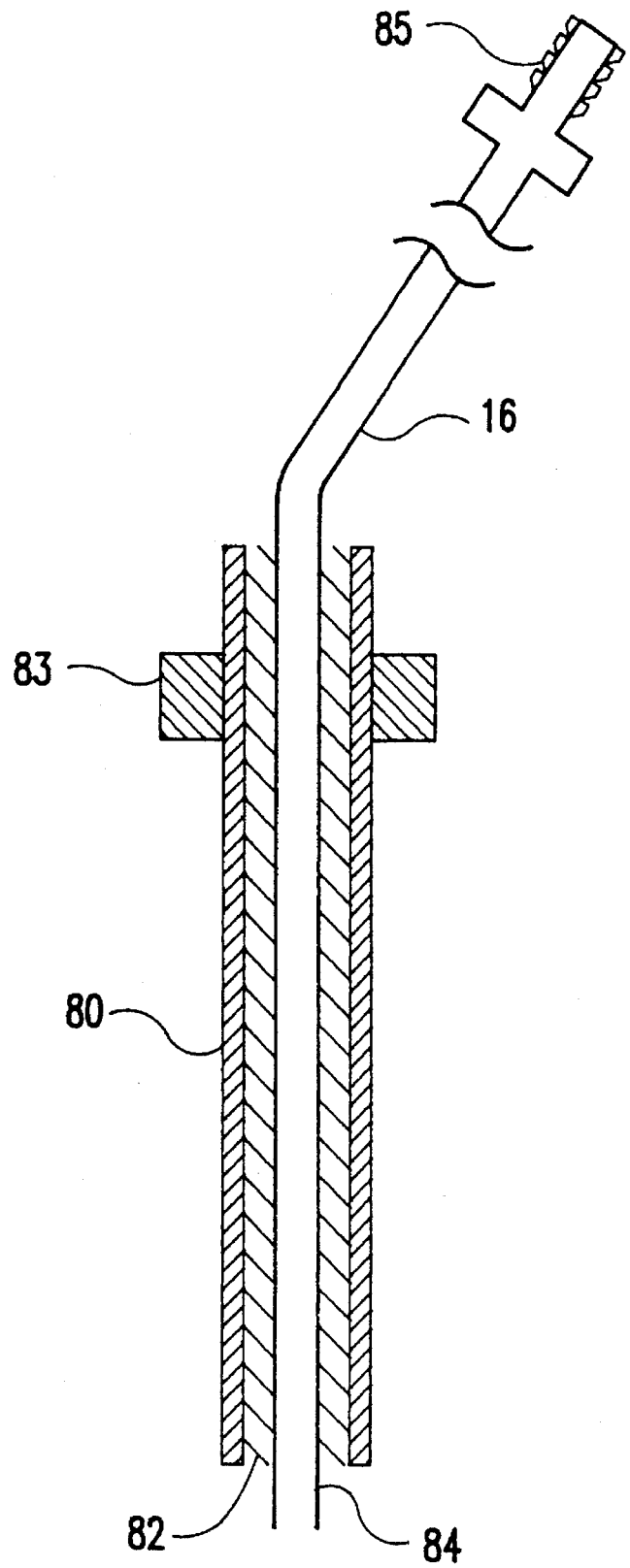
FIG. 3 is a schematic showing an experimental low carryover pipette probe.

Referring now to FIG. 3, there is shown a modified pipette tip design which consists of a stainless steel barrel 80 into which a contiguous length of 0.032" teflon tubing 16 is glued with an adhesive filler 82. The teflon tubing 16 serves as a liner for the entire length of barrel 80, and is of sufficient volume to contain all reagents and samples being pipetted. As such, no joints exist thereby eliminating interstitial spaces and exposed stainless steel. In addition, the barrel 80 is virtually immune to mechanical damage, and may be electrically connected to the pipetter arm 60 (FIG. 1) via mounting apparatus 83 to allow for capacitive level sensing. Capacitive level sensing involves measuring the capacitance between the probe tip and electrical ground through the liquid. This allows the volume of liquid in a tube and the depth of the probe to be determined.

Using the pipette probe tip shown in FIG. 3 along with Protocol B, an experimental carryover of 2.8 ppm was achieved. However, pipetting precision suffered somewhat and was reduced to about 4% CV with a 10 µL sample size. This problem is thought to exist because small droplets of excess fluid were carried from sample to sample at the interface 84 between the teflon tubing 16 and the stainless barrel 80.

Figure 4:
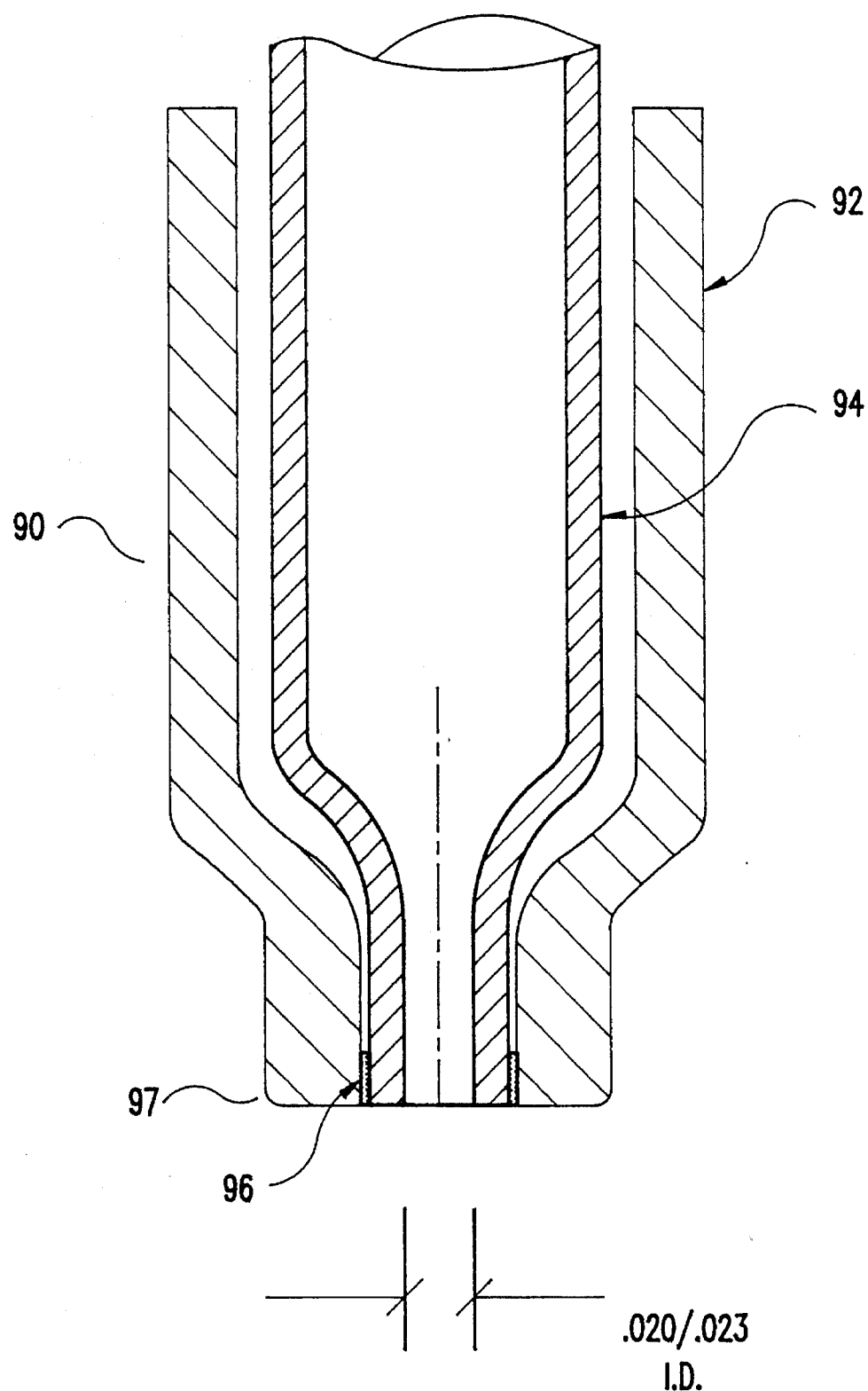
FIG. 4 is a schematic showing the low carryover pipette probe tip according to the present invention.

The final pipette probe design according to the present invention, is shown in FIG. 4. The probe 90 is a modified version of the probe shown in FIG. 3 and comprises a stainless steel barrel 92 having an exterior coating of polytetrafluoroethylene. A contiguous length of polytetrafluoroethylene tubing 94 runs coaxial within the barrel 92. In the preferred embodiment, the diameter of the polytetrafluoroethylene tubing 94 is 0.060", of course this measurement may be larger or smaller depending on the fluid requirements of the pipette probe 90. The pipette probe 90 is swaged at a fluid dispensing end 97 to a restrictive diameter. An adhesive seal 96 at the fluid dispensing end 97 adheres the polytetrafluoroethylene tube 94 to the barrel 92. In the preferred embodiment the polytetrafluoroethylene tube is swaged to between 0.020" and 0.023". This contributes to good precision in pipetting small fluid volumes, since any fluid droplets that may be retained at the tip after dispensing would be small in comparison to the total pipetted volume. Additionally, both the interior and the exterior of the tip 90 is polytetrafluoroethylene coated so as to reduce fluid droplet formation in the first place.

The pipette probe tip shown in FIG. 4 was determined to have a precision of less than 0.5% CV and 98% recovery accuracy, well within the acceptable range. In addition, a carryover of less than 2 ppm was achieved when using Protocol B and less than 5 ppm using Protocol C.

While the invention has been described in terms of a single preferred embodiment, those skilled in the art will recognize that the invention can be practiced with modification within the spirit and scope of the appended claims.

We claim:

1. A pipette probe for an automated chemical analyzer which reduces carryover contamination, comprising:

a rigid barrel having an interior surface and an exterior surface, said exterior surface being coated with a non-wettable material;

a contiguous section of polytetrafluoroethylene tube positioned coaxial within said barrel, said polytetrafluoroethylene tube having a fluid dispensing end and a connection end, said polytetrafluoroethylene tube and said barrel having a restricted diameter at said fluid dispensing end; and a seal means for attaching said interior surface of said barrel to said polytetrafluoroethylene tube at said fluid dispensing end, said non-wettable material and said contiguous section of polytetrafluoroethylene tube forming non-wettable surfaces which reduce carryover contamination by preventing fluid from adhering to the probe.

2. A pipette probe for an automated chemical analyzer which reduces carryover contamination, comprising:

a rigid, stainless steel barrel having an interior surface and an exterior surface, said exterior surface being coated with a non-wettable material;

a polytetrafluoroethylene tube positioned coaxial within said barrel, said polytetrafluoroethylene tube having a fluid dispensing end and a connection end, said polytetrafluoroethylene tube and said barrel having a restricted diameter at said fluid dispensing end; and a seal means for attaching said interior surface of said barrel to said polytetrafluoroethylene tube at said fluid dispensing end, said non-wettable material and said continuous section of polytetrafluoroethylene tube forming non-wettable surfaces which reduce carryover contamination by preventing fluid from adhering to the probe.

3. A pipette probe for an automated chemical analyzer as recited in claim 1 further comprising a mounting means for mounting said pipette probe to an automated chemical analyzer, said mounting means being electrically conductive to permit capacitive level sensing.

4. A pipette probe for an automated chemical analyzer as recited in claim 1 wherein said non-wettable material is polytetrafluoroethylene.

\* \* \* \* \*